(12) United States Patent
Reo

(10) Patent No.: US 8,361,154 B2
(45) Date of Patent: Jan. 29, 2013

(54) TEMPORARILY BOUND PROSTHETIC INTERVERTEBRAL DISCS IMPLANTABLE BY MINIMALLY INVASIVE SURGICAL TECHNIQUES

(75) Inventor: Michael L. Reo, Redwood City, CA (US)

(73) Assignee: Spinal Kinetics Inc., Sunnyvale, CA (US)

( * ) Notice: Subject to any disclaimer, the term of this patent is extended or adjusted under 35 U.S.C. 154(b) by 610 days.

(21) Appl. No.: 12/060,237

(22) Filed: Mar. 31, 2008

(65) Prior Publication Data

US 2009/0076611 A1 Mar. 19, 2009

Related U.S. Application Data

(60) Provisional application No. 60/909,454, filed on Mar. 31, 2007.

(51) Int. Cl.
*A61F 2/44* (2006.01)
(52) U.S. Cl. .............. 623/17.16; 623/17.15; 623/17.11
(58) Field of Classification Search ............. 623/17.15, 623/17.16
See application file for complete search history.

(56) References Cited

U.S. PATENT DOCUMENTS

| 5,824,093 | A | * | 10/1998 | Ray et al. | 623/17.16 |
| 6,110,210 | A | * | 8/2000 | Norton et al. | 623/17.16 |
| 2005/0228500 | A1 | * | 10/2005 | Kim et al. | 623/17.13 |

* cited by examiner

*Primary Examiner* — Thomas Barrett
*Assistant Examiner* — Christine Nelson
(74) *Attorney, Agent, or Firm* — E. Thomas Wheelock

(57) ABSTRACT

The described devices are bound spinal implants that may be surgically implanted into the spine to replace damaged or diseased discs using a posterior approach. The discs are prosthetic devices that approach or mimic the physiological motion and reaction of the natural disc.

16 Claims, 3 Drawing Sheets

Step (a)

Step (b)

TEMPORARILY BOUND PROSTHETIC INTERVERTEBRAL DISCS IMPLANTABLE BY MINIMALLY INVASIVE SURGICAL TECHNIQUES

RELATED APPLICATIONS

This application claims benefit from U.S. provisional patent application No. 60/909,454, filed Mar. 31, 2007, the entirety of which is incorporated by reference.

FIELD

The described devices are bound spinal implants that may be surgically implanted into the spine to replace damaged or diseased discs using a posterior approach. The discs are prosthetic devices that approach or mimic the physiological motion and reaction of the natural disc.

BACKGROUND

The intervertebral disc is an anatomically and functionally complex joint. The intervertebral disc is composed of three component structures: (1) the nucleus pulposus; (2) the annulus fibrosus; and (3) the vertebral end plates. The biomedical composition and anatomical arrangements within these component structures are related to the biomechanical function of the disc.

The spinal disc may be displaced or damaged due to trauma or a disease process. If displacement or damage occurs, the nucleus pulposus may herniate and protrude into the vertebral canal or intervertebral foramen. Such deformation is known as herniated or slipped disc. A herniated or slipped disc may press upon the spinal nerve that exits the vertebral canal through the partially obstructed foramen, causing pain or paralysis in the area of its distribution.

To alleviate this condition, it may be necessary to remove the involved disc surgically and fuse the two adjacent vertebrae. In this procedure, a spacer is inserted in the place originally occupied by the disc and the spacer is secured between the neighboring vertebrae by the screws and plates or rods attached to the vertebrae. Despite the excellent short-term results of such a "spinal fusion" for traumatic and degenerative spinal disorders, long-term studies have shown that alteration of the biomechanical environment leads to degenerative changes particularly at adjacent mobile segments. The adjacent discs have increased motion and stress due to the increased stiffness of the fused segment. In the long term, this change in the mechanics of the motion of the spine causes these adjacent discs to degenerate.

Artificial intervertebral replacement discs may be used as an alternative to spinal fusion.

SUMMARY

Prosthetic intervertebral discs and methods for using such discs are described. The subject prosthetic discs include an upper end plate, a lower end plate, and a compressible core member disposed between the two end plates. The described prosthetic discs have shapes, sizes, and other features that are particularly suited for implantation using minimally invasive surgical procedures, particularly from a posterior approach. In particular, the described discs are releasably bound with an elongate member, e.g., string, cable, wire, etc., to allow remotely controlled expansion of a bound disc. Such elongate member may be a releasable binding element wrapped through the end plates that compresses at least some portion of the disc to a lower height or profile for implantation. Release of the binding element allows expansion of the compressed disc.

The described bound prosthetic discs include top and bottom end plates separated by one or more compressible core members. I also refer to the top and bottom end plates as first and second end plates, particularly since the nature of this device is such that it operates the same way without regard to the orientation of the device. The two plates may be held together by at least one fiber wound around at least one region of the top end plate and at least one region of the bottom end plate. The described discs may include integrated vertebral body fixation elements. When considering a lumbar disc replacement from the posterior access, the two plates are preferably elongated, having a length that is substantially greater than its width. Typically, the dimensions of the prosthetic discs range in height from 8 mm to 15 mm; the width ranges from 6 mm to 13 mm. The height of the prosthetic discs ranges from 9 mm to 11 mm. The widths of the disc may be 10 mm to 12 mm. The length of the prosthetic discs may range from 18 mm to 30 mm, perhaps 24 mm to 28 mm. Typical shapes include oblong, bullet-shaped, lozenge-shaped, rectangular, or the like.

The described bound disc structures may be held together by at least one fiber wound around at least one region of the upper end plate and at least one region of the lower end plate. The fibers are generally high tenacity fibers with a high modulus of elasticity. The elastic properties of the fibers, as well as factors such as the number of fibers used, the thickness of the fibers, the number of layers of fiber windings in the disc, the tension applied to each layer, and the crossing pattern of the fiber windings enable the prosthetic disc structure to mimic the functional characteristics and biomechanics of a normal-functioning, natural disc.

A number of conventional surgical approaches may be used to place a pair of prosthetic discs. Those approaches include a modified posterior lumbar interbody fusion (PLIF) and a modified transforaminal lumbar interbody fusion (TLIF) procedures. We also describe apparatus and methods for implanting prosthetic intervertebral discs using minimally invasive surgical procedures. In one variation, the apparatus includes a pair of cannulae that are inserted posteriorly, side-by-side, to gain access to the spinal column at the disc space. A pair of prosthetic discs may then be implanted by way of the cannulae to be located between two vertebral bodies in the spinal column.

The prosthetic discs may be configured by selection of sizes and structures suitable for implantation by minimally invasive procedures. The discs may be bound, perhaps in a compressed condition or specific form, by one or more elongate members, e.g., string, cable, wire, etc. that may tied to remotely allow release of the disc.

Other and additional devices, apparatus, structures, and methods are described by reference to the drawings and detailed descriptions below.

BRIEF DESCRIPTION OF THE DRAWINGS

The Figures contained herein are not necessarily drawn to scale. Some components and features may be exaggerated for clarity.

DETAILED DESCRIPTION

Described below are prosthetic intervertebral discs, methods of using such discs, apparatus for implanting such discs, and methods for implanting such discs. It is to be understood that the prosthetic intervertebral discs, implantation apparatus, and methods are not limited to the particular embodiments described, as these may, of course, vary. It is also to be understood that the terminology used here is only for the purpose of describing particular embodiments, and is not intended to be limiting in any way.

Insertion of the prosthetic discs may be approached using modified conventional procedures, such as a posterior lumbar interbody fusion (PLIF) or transforaminal lumbar interbody fusion (TLIF). In the modified PLIF procedure, the spine is approached via midline incision in the back. The erector spinae muscles are stripped bilaterally from the vertebral lamina at the required levels. A laminectomy is then performed to further allow visualization of the nerve roots. A partial facetectomy may also be performed to facilitate exposure. The nerve roots are retracted to one side and a discectomy is performed. Optionally, a chisel may then used to cut one or more grooves in the vertebral end plates to accept the fixation components on the prostheses. Appropriately-sized prostheses may then be inserted into the intervertebral space on either side of the vertebral canal.

In a modified TLIF procedure, the approach is also posterior, but differs from the PLIF procedure in that an entire facet joint is removed and the access is only on one side of the vertebral body. After the facetectomy, the discectomy is performed. Again, a chisel may be used to create on or more grooves in the vertebral end plates to cooperatively accept the fixation components located on each prosthesis. The prosthetic discs may then be inserted into the intervertebral space. One prosthesis may be moved to the contralateral side of the access and then a second prosthesis then inserted on the access side.

It should be apparent that we refer to these procedures as "modified" in that neither procedure is used to "fuse" the two adjacent vertebrae.

Figure 1:
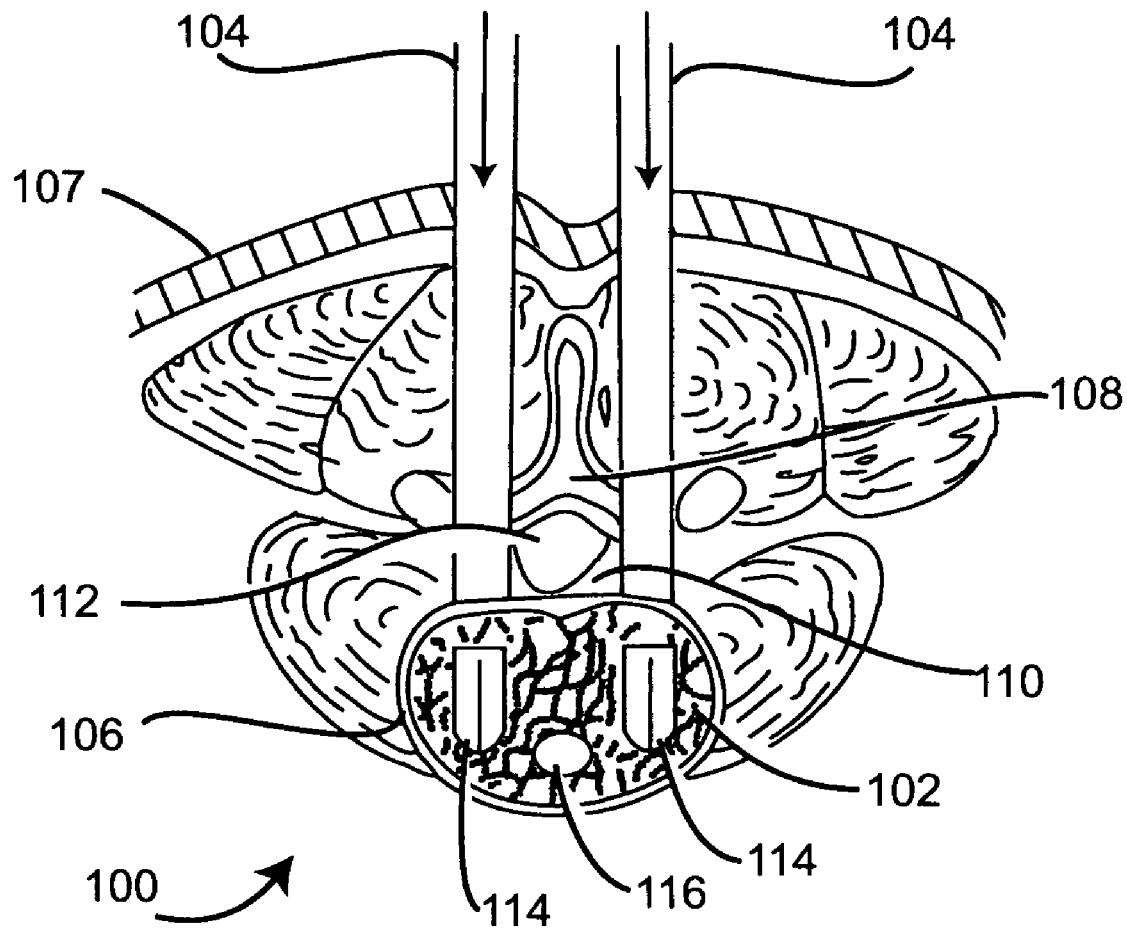
FIG. 1 shows a method for placement of prosthetic intervertebral discs using a posterior approach.

FIG. 1 shows a top, cross section view of a spine (100), sectioned across an intervertebral disc (102). This Figure depicts a minimally invasive surgical procedure for implanting a pair of intervertebral discs in an intervertebral region formed by the removal of a natural disc. This minimally invasive surgical implantation method is performed using a posterior approach, rather than the conventional anterior lumbar disc replacement surgery or the modified PLIF and TLIF procedures described above.

In FIG. 1, two cannulae (104) are inserted posteriorly, through the skin (107), to provide access to the spinal column. More particularly, a small incision is made and a pair of access windows created through the lamina (106) of one of the vertebrae (108) on each side of the vertebral canal (110) to access the natural vertebral disc. The spinal cord (112) and nerve roots are avoided or moved to provide access. Once access is obtained, the two cannulae (104) are inserted. The cannulae (104) may be used as access passageways in removing the natural disc with conventional surgical tools. Alternatively, the natural disc may be removed prior to insertion of the cannulae. The cannulae are also used to introduce the prosthetic intervertebral discs (114) to the intervertebral region.

The described bound prosthetic discs are of a design and capability such that they may be employed at more than one level, i.e., disc location, in the spine. Specifically, several natural discs may be replaced with my discs. As will be described in greater detail below, each such level will be implanted with at least two of my discs. Kits, containing two of my discs for a single disc replacement or four of my discs for replacement of discs at two levels in the spine, perhaps with sterile packaging are contemplated. Such kits may also contain one or more cannulae having a central opening allowing passage and implantation of my discs.

Once the natural disc has been removed and the cannulae (104) located in place, a pair of prosthetic discs (114) is implanted between adjacent vertebral bodies. The prosthetic discs have a shape and size suitable making them useful with (or adapted for) various minimally invasive procedures. The discs may have a shape such as the elongated one-piece prosthetic discs described below.

A prosthetic disc (114) is guided through each of the cannula such that each of the prosthetic discs (114) is implanted between the two adjacent vertebral bodies. The two prosthetic discs (114) may be located side-by-side and spaced slightly apart, as viewed from above. Optionally, prior to implantation, grooves may be formed on the internal surfaces of one or both of the vertebral bodies in order to engage anchoring components or features located on or integral with the prosthetic discs (114). The grooves may be formed using a chisel tool adapted for use with the minimally invasive procedure, i.e., adapted to extend through a relatively small access space (such as the tunnel-like opening found in through the cannulae) and to chisel the noted grooves within the intervertebral space present after removal of the natural disc.

These discs may be used as shown in FIG. 1 or, optionally, they may be implanted with an additional prosthetic disc or discs, perhaps in the position shown for auxiliary disc (116).

Additional prosthetic discs may also be implanted in order to obtain desired performance characteristics, and the implanted discs may be implanted in a variety of different relative orientations within the intervertebral space. In addition, the multiple prosthetic discs may each have different performance characteristics. For example, a prosthetic disc to be implanted in the central portion of the intervertebral space may be configured to be more resistant to compression than one or more prosthetic discs that are implanted nearer the outer edge of the intervertebral space. For instance, the stiffness of the outer discs (e.g., 114) may each be configured such that those outer discs exhibit approximately 5% to 80% of the stiffness of the central disc (116), perhaps in the range of about 30% to 60% of the central disc (116) stiffness. Other performance characteristics may be varied as well.

This description may describe a number of variations of prosthetic intervertebral discs. By "prosthetic intervertebral disc" is meant an artificial or manmade device that is so configured or shaped that it may be employed as a total or partial replacement of an intervertebral disc in the spine of a vertebrate organism, e.g., a mammal, such as a human. The described prosthetic intervertebral discs have dimensions that permit them, either alone or in combination with one or more other prosthetic discs, to substantially occupy the space between two adjacent vertebral bodies that is present when the naturally occurring disc between the two adjacent bodies is removed, i.e., a void disc space. By "substantially occupy"

is meant that, in the aggregate, the discs occupy at least about 30% by surface area, perhaps at least about 80% by surface area or more. The subject discs may have a roughly bullet or lozenge shaped structure adapted to facilitate implantation by minimally invasive surgical procedures.

The discs may include both an upper (or top) and lower (or bottom) end plate, where the upper and lower end plates are separated from each other by a compressible element such as one or more core members, where the combination structure of the end plates and compressible element provides a prosthetic disc that functionally approaches or closely mimics a natural disc. The top and bottom end plates may be held together by at least one fiber attached to or wound around at least one portion of each of the top and bottom end plates. As such, the two end plates (or planar substrates) are held to each other by one or more fibers that are attached to or wrapped around at least one domain, portion, or area of the upper end plate and lower end plate such that the plates are joined to each other.

FIG. 2 shows a variation of my bound prosthetic intervertebral disc (200). This variation comprises an upper end plate (202) and a lower end plate (204) separated by a compressible core (206). As discussed below in more detail, the compressible core (206) may comprise one or more core members (not shown) and be bounded by one or more fibers (207) extending between the upper end plate (202) and the lower end plate (204). The upper and lower end plates (202, 204) may include apertures (not shown), through which the fibers (207) may pass. Other components (woven or nonwoven fabrics, wires, etc.) may be used in functional substitution for the fibers (207).

Also included in this variation is a binding element (210) that passes from the proximal end (212), through a passageway (214) inset into lower end plate (204), out the distal end (216), through an opening (218), and back through the passageway (214) to the starting point. When both ends of the binding element (210) are held taut, the distal end (216) of the disc (200) is compressed. Release of the binding element and its withdrawal through the pathway, releases the compression of the disc and allows it to expand to its normal height.

Figure 2A:
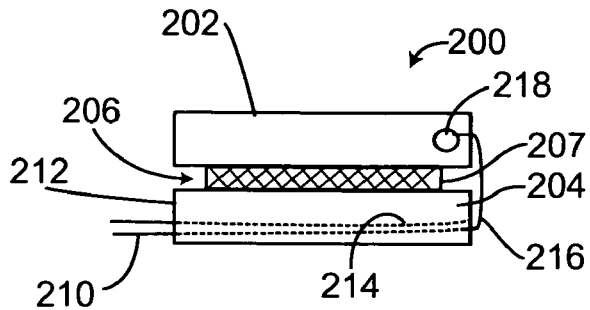
FIG. 2A is a side view of one variation of my bound prosthetic disc.
Figure 2B:
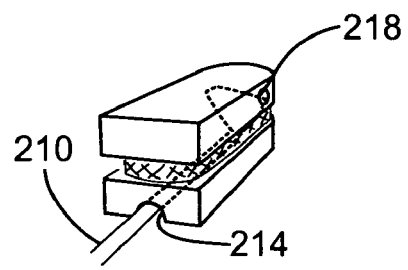
FIG. 2B is a perspective view of the variation seen in FIG. 2A.

FIG. 2B shows a perspective view of the disc shown in FIG. 2A. The pathway of the binding element (210) through the disc (200) is shown (in shadow)—passing back and forth through the passageway (214) and through the distal opening (218).

The utility of the binding element shown in the various incarnations described here is multiple. First, the profile (or height) of the disc is minimized for enhancing the ability of the user to easily and accurately place the prosthetic disc in the prepared intervertebral space. Some commercial prosthetic discs are not at all compressible, a factor that limits those discs' suitability for many situations. The lower profile is better able to pass through small access points into the intervertebral space. This allows the physician to utilize accesses, e.g., through spinal ligaments, that are smaller. The narrow form factor of the described discs combined with the binding element allows, in some variations, the physician to introduce the prosthetic disc "vertically" through a narrower ligament opening and then to rotate it into placement position. The user's ability to situate the bound prosthetic disc in the intervertebral space with a simple grasping tool and then to release the binding element by a simple pull to finally place the disc in its final implantation site is significant. The ease of "tool use" is a very positive attribute. The form of the binding element may be tailored for specific situations. In particular, the binding element may be attached in such a way that only one end of the prosthetic disc is compressed, e.g., see FIGS. 2A, 2B, and 3. The binding element may be attached to provide differential compression, e.g., wherein one end of the disc is compressed more than is the other.

Figure 3:
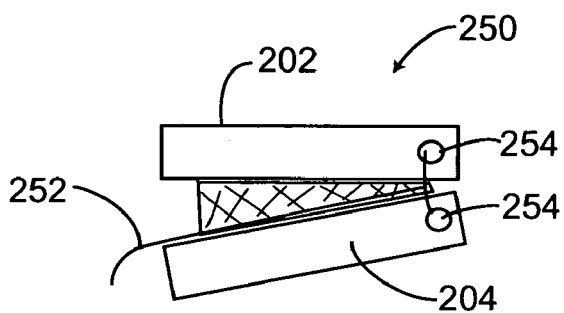
FIG. 3 is a side view of another variation of my bound prosthetic disc.

FIG. 3 is a side view of another variation of my device (250) showing the binding element (252). The binding element (252) passes through a pair of openings (254) in the distal end of the upper and lower end plates (202, 204). This arrangement provides an angle between those end plates.

Figure 4:
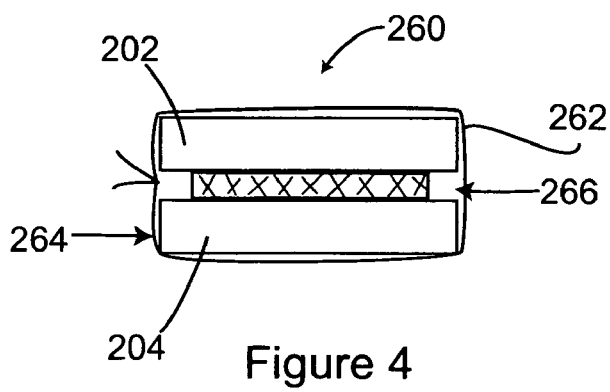
FIG. 4 is a side view of another variation of my bound prosthetic disc.

FIG. 4 is a side view of another variation of my disc (260), in this instance providing an example of a binding element (260) around the disc and extending from the proximal end (264) of the disc to the distal end (266) of the disc and then back. This arrangement can provide full compression to the disc, both in the sense that the disc is able to achieve the lowest possible height and also that the compression is achievable along the complete length (distal-proximal) of the disc.

Figure 5:
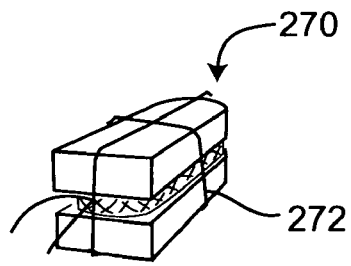
FIG. 5 is a perspective view of another variation of my bound prosthetic disc.

FIG. 5 shows a further variation of my bound prosthetic disc (270) having a binding element (272) that envelopes the disc in two axes, from side-to-side and from distal to proximal. In this and in all of the variations shown herein, the designer may choose to use more than one binding element on a single disc. For instance, the variations shown in FIGS. 2A, 2B, and 3 may also include an additional, separate binding element at the other non-bound end so that the two binding elements may be separately released allowing differential expansion (distal-proximal) for even more control during placement in the intervertebral space.

The binding element may be made from a wide variety of materials. Suitable materials include synthetic polymers, natural polymers (e.g., silk), metals, alloys (including superelastic alloys such as nitinol), coated materials (e.g., lubricious polymers on "strength" polymers, lubricious polymers on metals or alloys, etc.), and the like. The form of the binding element may be a monofilament, thread or multifilament, cable, etc.

The release mechanism for each of these variations may be any of a variety of slip knots (with safety lines, if desired), crimpings, twisted wire, etc.

The end plates may be planar substrates having a length of from about 12 mm to about 45 mm, such as from about 13 mm to about 44 mm, a width of from about 11 mm to about 28 mm, such as from about 12 mm to about 25 mm, and a thickness of from about 0.5 mm to about 5 mm, such as from about 1 mm to about 3 mm. The top and bottom end plates are fabricated or formed from a physiologically acceptable material that provides for the requisite mechanical properties, primarily structural rigidity and durability. Representative materials from which the end plates may be fabricated are known to those of skill in the art and include: metals such as titanium, titanium alloys, stainless steel, cobalt/chromium, etc.; plastics such as polyethylene with ultra high molar mass (molecular weight) (UHMW-PE), polyether ether ketone (PEEK), etc.; ceramics; graphite; etc.

The discs may also include fibers wound between and connecting the upper and lower end plates. These fibers may extend through a plurality of openings or apertures formed on portions of each of the upper and lower end plates. Thus, a fiber extends between the pair of end plates, and extends up through an aperture in the upper end plate and back down through an adjacent aperture in that end plate. The fibers need not be tightly wound, thereby allowing a degree of axial rotation, bending, flexion, and extension by and between the end plates. The amount of axial rotation generally is in the range from about 0° to about 15°, perhaps from about 2° to 10°. The amount of bending generally has a range from about 0° to about 18°, perhaps from about 2° to 15°. The amount of flexion and extension generally has a range from about 0° to about 25°, perhaps from about 3° to 15°. Of course, the fibers may be more or less tightly wound to vary the resultant values of these rotational values. The core members forming compressible core may be provided in an uncompressed or in a compressed state. An annular capsule may be included in the space between the upper and lower end plates surrounding the compressible core.

My described prosthetic discs may include a compressible core comprising a larger single elongated core member, a generally circular core member, or two or more generally cylindrical core members. The dual core structure may better simulate the performance characteristics of a natural disc. In addition, the fibers found in the dual core structure are believed to endure less stress relative to the fibers found in the single core structure.

The lateral, or horizontal, surface area of each of the end plates—i.e., the area of the disc surfaces that engage the vertebral bodies—is substantially larger than the cross-sectional surface area of the core member or members. The cross-sectional surface area of the core member or members may be from about 5% to about 80% of the cross-sectional area of a given end plate, perhaps from about 10% to about 60%, or from about 15% to about 50%. In this way, for a given compressible core having sufficient compression, flexion, extension, rotation, and other performance characteristics but having a relatively small cross-sectional size, the core member may be used to support end plates having a relatively larger cross-sectional size in order to help prevent subsidence into the vertebral body surfaces. In the variations described here, the compressible core and end plates also have a size that is appropriate for or adapted for implantation by way of posterior access or minimally invasive surgical procedures, such as those described above.

Figure 6:
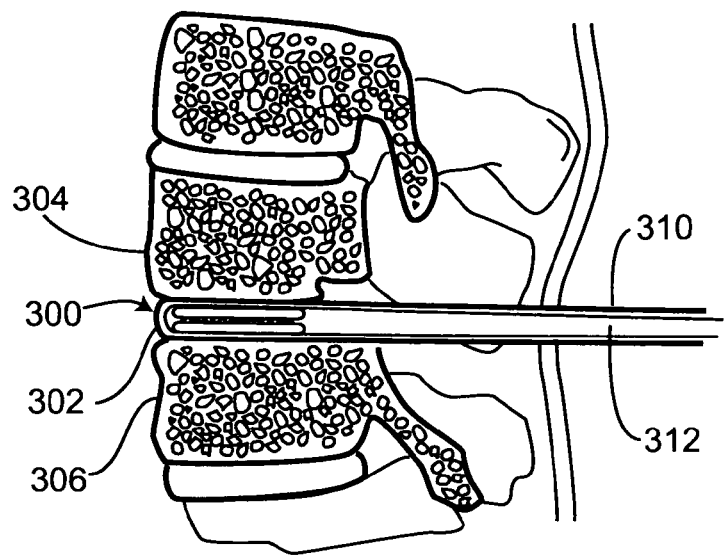
FIG. 6 schematically illustrates a method for implanting the described prosthetic discs.
Figure 6:
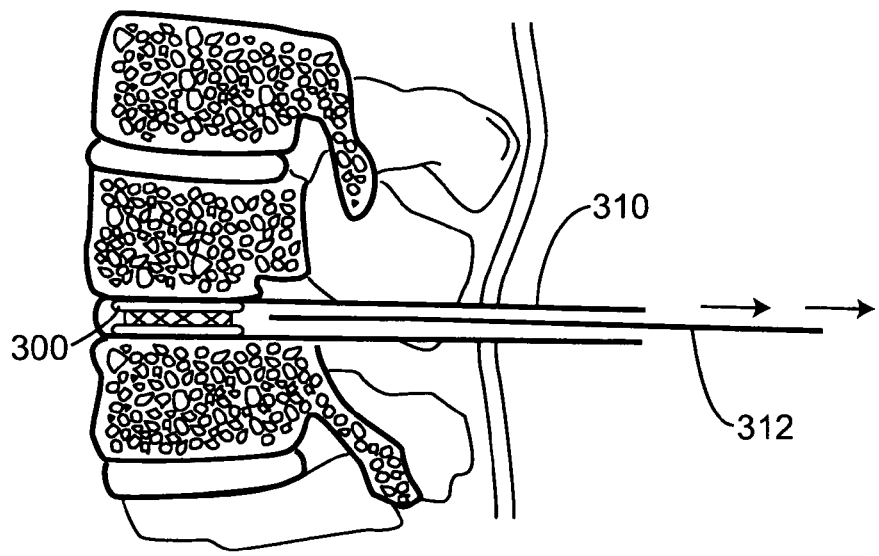

FIG. 6, step (a), shows the placement of a compressed disc (300) into the intervertebral space (302) between an upper vertebra (304) and the adjacent lower vertebra (306). No placement tool is shown, for ease of explanation. The compressed disc (300) has been passed through the cannula (310) to the implantation site with a binding element (312) in place.

FIG. 6, step (b), shows the disc (300) after removal of the binding element (312) and expansion of the disc. The cannula (310) and the binding element (312) are shown being removed.

Each of the described prosthetic discs depicted in the Figures has a greater length than width. The aspect ratio (length: width) of the discs may be about 1.5:1 to 5.0:1, perhaps about 2.0:1 to 4.0:1, or about 2.5:1 to 3.5:1. Exemplary shapes to provide these relative dimensions include rectangular, oval, bullet-shaped, lozenge-shaped, and others. These shapes facilitate implantation of the discs by the minimally invasive procedures described above. Of course, the shape of my discs is not limited to those listed just above, but may be any shape suitable for use as all or part of a complete intervertebral prosthetic disc.

The surfaces of the upper and lower end plates, i.e., those surfaces in contact with and eventually adherent to the respective opposed bony surfaces of the upper and lower vertebral bodies, may have one or more anchoring or fixation components or mechanism for securing those end plates to the vertebral bodies. For example, the anchoring feature may be one or more "keels," a fin-like extension often having a substantially triangular cross-section and having a sequence of exterior barbs or serrations. This anchoring component is intended to cooperatively engage a mating groove that is formed on the surface of the vertebral body and to thereby secure the end plate to its respective vertebral body. The serrations enhance the ability of the anchoring feature to engage the vertebral body.

Further, this variation of the anchoring component may include one or more holes, slots, ridges, grooves, indentations, or raised surfaces to further assist in anchoring the disc to the associated vertebra. These physical features will so assist by allowing for bony ingrowth. Each end plate may have a different number of anchoring components, and those anchoring features may have a different orientation on each end plate. The number of anchoring features generally ranges in number from about 0 to about 500, perhaps from about 1 to 10. Alternatively, another fixation or anchoring mechanism may be used, such as ridges, knurled surfaces, serrations, or the like. In some variations, the discs will have no external fixation mechanism. In such variations, the discs are held in place laterally by the friction forces between the disc and the vertebral bodies.

Further, each of the described variations may additionally include a porous covering or layer (e.g., sprayed Ti metal) allowing boney ingrowth and may include some osteogenic materials.

As noted above, in the variations shown herein, the upper end plate and lower end plate may each contain a plurality of apertures through which the fibers may be passed through or wound, as shown. The actual number of apertures contained on an end plate is variable. Increasing the number of apertures allows an increase in the circumferential density of the fibers holding the end plates together. The number of apertures may range from about 3 to 100, perhaps in the range of 10 to 30. In addition, the shape of the apertures may be selected so as to provide a variable width along the length of the aperture. For example, the width of the apertures may taper from a wider inner end to a narrow outer end, or visa versa. Additionally, the fibers may be wound multiple times within the same aperture, thereby increasing the radial density of the fibers. In each case, this improves the wear resistance and increases the torsional and flexural stiffness of the prosthetic disc, thereby further approximating natural disc stiffness. In addition, the fibers may be passed through or wound on each aperture, or only on selected apertures, as needed. The fibers may be wound in a uni-directional manner, where the fibers are wound in the same direction, e.g., clockwise, which closely mimics natural annular fibers found in a natural disc, or the fibers may be wound bi-directionally. Other winding patterns, both single and multi-directional, may also be used.

The apertures provided in the various end plates discussed here, may be of a number of shapes. Such aperture shapes include slots with constant width, slots with varying width, openings that are substantially round, oval, square, rectangular, etc. Elongated apertures may be radially situated, circumferentially situated, spirally located, or combinations of these shapes. More than one shape may be utilized in a single end plate.

One purpose of the fibers is to hold the upper and lower end plates together and to limit the range-of-motion to mimic or at least to approach the range-of-motion of a natural disc. The fibers may comprise high tenacity fibers having a high modulus of elasticity, for example, at least about 100 MPa, perhaps at least about 500 MPa. By high tenacity fibers is meant fibers able to withstand a longitudinal stress of at least 50 MPa, and perhaps at least 250 MPa, without tearing. The fibers 207 are generally elongate fibers having a diameter that ranges from about 100 μm to about 1000 μm, and preferably about 200 μm to about 400 μm. The fibrous components may be single strands or, more typically, multi-strand assemblages. Optionally, the fibers may be injection molded or otherwise coated with an elastomer to encapsulate the fibers, thereby providing protection from tissue ingrowth and improving torsional and flexural stiffness. The fibers may be coated with one or more other materials to improve fiber stiffness and wear. Additionally, the core may be injected with a wetting agent such as saline to wet the fibers and facilitate the mimicking of the viscoelastic properties of a natural disc. The fibers may comprise a single or multiple component fibers.

The fibers may be fabricated from any suitable material. Examples of suitable materials include polyesters (e.g., Dacron® or the Nylons), polyolefins such as polyethylene, polypropylene, low-density and high density polyethylenes, linear low-density polyethylene, polybutene, and mixtures and alloys of these polymers. HDPE and UHMWPE are especially suitable. Also suitable are various polyaramids, poly-paraphenylene terephthalamide (e.g., Kevlar®), carbon or glass fibers, various stainless steels and superelastic alloys (such as nitinol), polyethylene terephthalate (PET), acrylic polymers, methacrylic polymers, polyurethanes, polyureas, other polyolefins (such as polypropylene and other blends and olefinic copolymers), halogenated polyolefins, polysaccharides, vinylic polymers, polyphosphazene, polysiloxanes, liquid crystal polymers such as those available under the tradename VECTRA, polyfluorocarbons such as polytetrafluoroethylene and e-PTFE, and the like.

The fibers may be terminated on an end plate in a variety of ways. For instance, the fiber may be terminated by tying a knot in the fiber on the superior or inferior surface of an end plate. Alternatively, the fibers may be terminated on an end plate by slipping the terminal end of the fiber into an aperture on an edge of an end plate, similar to the manner in which thread is retained on a thread spool. The aperture may hold the fiber with a crimp of the aperture structure itself, or by an additional retainer such as a ferrule crimp. As a further alternative, tab-like crimps may be machined into or welded onto the end plate structure to secure the terminal end of the fiber. The fiber may then be closed within the crimp to secure it. As a still further alternative, a polymer may be used to secure the fiber to the end plate by welding, including adhesives or thermal bonding. That terminating polymer may be of the same material as the fiber (e.g., UHMWPE, PE, PET, or the other materials listed above). Still further, the fiber may be retained on the end plates by crimping a cross-member to the fiber creating a T-joint, or by crimping a ball to the fiber to create a ball joint.

The core members provide support to and maintain the relative spacing between the upper and lower end plates. The core members may comprise one or more relatively compliant materials. In particular, the compressible core members in this variation and the others discussed herein, may comprise a thermoplastic elastomer (TPE) such as a polycarbonate-urethane TPE having, e.g., a Shore value of 50D to 60D, e.g. 55D. An example of such a material is the commercially available TPE, BIONATE. Shore hardness is often used to specify flexibility or flexural modulus for elastomers.

We have had success with core members comprising TPE that are compression molded at a moderate temperature from an extruded plug of the material. For instance, with the polycarbonate-urethane TPE mentioned above, a selected amount of the polymer is introduced into a closed mold upon which a substantial pressure may be applied, while heat is applied. The TPE amount is selected to produce a compression member having a specific height. The pressure is applied for 8-15 hours at a temperature of 70-90° C., typically about 12 hours at 80° C.

Other examples of suitable representative elastomeric materials include silicone, polyurethanes, polybutylene terephthalate (PBT), polybutylene glycol (polytetramethylene oxide or PMTO), polyesters (e.g., Hytrel®), their mixtures or the like.

Compliant polyurethane elastomers are discussed generally in, M. Szycher, J. Biomater. Appl. "Biostability of polyurethane elastomers: a critical review", 3(2):297 402 (1988); A. Coury, et al., "Factors and interactions affecting the performance of polyurethane elastomers in medical devices", J. Biomater. Appl. 3(2):130 179 (1988); and Pavlova M, et al., "Biocompatible and biodegradable polyurethane polymers", Biomaterials 14(13):1024 1029 (1993). Examples of suitable polyurethane elastomers include aliphatic polyurethanes, segmented polyurethanes, hydrophilic polyurethanes, polyether-urethane, polycarbonate-urethane, and silicone-polyether-urethane.

Other suitable elastomers include various polysiloxanes (or silicones), copolymers of silicone and polyurethane, polyolefins, thermoplastic elastomers (TPE's) such as atactic polypropylene, block copolymers of styrene and butadiene (e.g., SBS rubbers), polyisobutylene, and polyisoprene, neoprene, polynitriles, artificial rubbers such as produced from copolymers produced of 1-hexene and 5-methyl-1,4-hexadiene.

One variant of the construction for the core member comprises a nucleus formed of a hydrogel and an elastomer reinforced fiber annulus.

For example, the nucleus, the central portion of the core member, may comprise a hydrogel material. Hydrogels are water-swellable or water-swollen polymeric materials typically having structures defined either by a crosslinked or an interpenetrating network of hydrophilic homopolymers or copolymers. In the case of physical crosslinking, the linkages may take the form of entanglements, crystallites, or hydrogen-bonded structures to provide structure and physical integrity to the polymeric network.

Suitable hydrogels may be formulated from a variety of hydrophilic polymers and copolymers including polyvinyl alcohol, polyethylene glycol, polyvinyl pyrrolidone, polyethylene oxide, polyacrylamide, polyurethane, polyethylene oxide-based polyurethane, and polyhydroxyethyl methacrylate, and copolymers and mixtures of the foregoing.

Silicone-base hydrogels are also suitable. Silicone hydrogels may be prepared by polymerizing a mixture of monomers including at least one silicone-containing monomer and or oligomer and at least one hydrophilic co-monomer such as N-vinyl pyrrolidone (NVP), N-vinylacetamide, N-vinyl-N-methyl acetamide, N-vinyl-N-ethyl acetamide, N-vinylformamide, N-vinyl-N-ethyl formamide, N-vinylformamide, 2-hydroxyethyl-vinyl carbonate, and 2-hydroxyethyl-vinyl carbamate (beta-alanine).

The annulus may comprise an elastomer, such as those discussed just above, reinforced with a fiber.

The fiber may be wrapped around the core member in a variety of different configurations, e.g., wrapping the core member in a random pattern, circumferential wrapping, radial wrapping, progressive polar (or near-polar) wrapping moving around the core, and combinations of these patterns and with other patterns.

The shape of each of the core members may be cylindrical, although the shape (as well as the materials making up the core member and the core member size) may be varied to obtain desired physical or performance properties. For example, the core member's shape, size, and materials will directly affect the degree of flexion, extension, lateral bending, and axial rotation of the prosthetic disc.

The annular capsule may be made of an appropriate polymer, such as polyurethane or silicone or the materials discussed above, and may be fabricated by injection molding, two-part component mixing, or dipping the end plate-core-fiber assembly into a polymer solution. The annular capsule may be oblong with straight sidewalls or with one or more bellows formed in the sidewalls. A function of the annular capsule is to act as a barrier that keeps the disc materials (e.g., fiber strands) within the body of the disc, and that keeps potential, natural in-growth outside the disc.

Where a range of values is provided, it is understood that each intervening value within the range, to the tenth of the unit of the lower limit (unless the context clearly dictates otherwise), between the upper and lower limit of that range and any other stated or intervening value in that stated range is described. The upper and lower limits of these smaller ranges may independently be included in the smaller ranges is also described, subject to any specifically excluded limit in the stated range. Where the stated range includes one or both of the limits, ranges excluding either or both of those included limits are also described.

Unless defined otherwise, all technical and scientific terms used herein have the same meaning as commonly understood by one of ordinary skill in the medical devices art. Although methods and materials similar or equivalent to those described here may also be used in the practice or testing of the described devices and methods, the preferred methods and materials are described in this document. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

As will be apparent to those of skill in the art upon reading this disclosure, each of the individual variations described and illustrated herein has discrete components and features which may be readily separated from or combined with the features of any of the other several embodiments without departing from the scope or spirit of this disclosure. For example, and without limitation, several of the variations described here include descriptions of anchoring features, protective capsules, fiber windings, and protective covers covering exposed fibers for integrated end plates. It is expressly contemplated that these features may be incorporated (or not) into those variations in which they are not shown or described.

All patents, patent applications, and other publications mentioned herein are hereby incorporated herein by reference in their entireties. The patents, applications, and publications discussed herein are provided solely for their disclosure prior to the filing date of the present application. Nothing herein is to be construed as an admission that contents of those patents, applications, and publications are "prior" as that term is used in the Patent Law.

The preceding merely illustrates the principles of the invention. It will be appreciated that those skilled in the art will be able to devise various arrangements which, although not explicitly described or shown herein, embody the principles otherwise described here and are included within its spirit and scope. Furthermore, all examples and conditional language recited herein are principally intended to aid the reader in understanding the described principles of my devices and methods. Moreover, all statements herein reciting principles, aspects, and variation as well as specific examples thereof, are intended to encompass both structural and functional equivalents. Additionally, it is intended that such equivalents include both currently known equivalents and equivalents developed in the future, i.e., any elements developed that perform the same function, regardless of structure.

What is claimed is:

1. A prosthetic intervertebral disc for insertion into an intervertebral space, comprising:
   a. a first end plate;
   b. a second end plate;
   c. at least one compressible core member positioned between said first and second end plates;
   d. at least one fiber extending between and engaged with said first and second end plates; and
   e. at least one releasable binding element compressing at least a portion of the disc to a lower height and releasable after insertion of the disc into the intervertebral space to release said compression, and
   wherein said end plates and said core member are held together by said at least one fiber.

2. The prosthetic intervertebral disc of claim 1 wherein the at least one binding element compresses an end of the disc.

3. The prosthetic intervertebral disc of claim 1 wherein one binding element compresses an end of the disc.

4. The prosthetic intervertebral disc of claim 1 wherein two binding elements compress a first end and a second end of the disc.

5. The prosthetic intervertebral disc of claim 1 wherein the at least one binding element compresses a first end and a second end of the disc.

6. The prosthetic intervertebral disc of claim 1 wherein the at least one binding element comprises a composition selected from synthetic polymers, natural polymers, metals, alloys, and coated materials.

7. The prosthetic intervertebral disc of claim 1 wherein the at least one binding element comprises a form selected from monofilament, thread, multifilament, and cable.

8. The prosthetic intervertebral disc of claim 1 wherein the disc is bullet-shaped.

9. The prosthetic intervertebral disc of claim 1 wherein the disc is lozenge-shaped.

10. The prosthetic intervertebral disc of claim 1, wherein the at least one fiber is engaged with said first and second end plates because the at least one fiber is wound around at least one portion of said first end plate and at least one portion of said second end plate.

11. The prosthetic intervertebral disc of claim 1, wherein the at least one releasable binding element is placed under tension to compress at least the portion of the disc to the lower height.

12. The prosthetic intervertebral disc of claim 11, wherein the at least one releasable binding element is one of a string, cable, or wire.

13. A kit for surgically replacing a disc in a spine with a posterior approach, comprising exactly two of the prosthetic discs of claim 1.

14. The kit of claim 13 further comprising at least one cannula suitable for a posterior approach configured to access a disc to be replaced and to bypass the spinal cord and local nerve roots and further sized for passage of at least one of the two prosthetic discs of claim 1.

15. The kit of claim 13 wherein the first and second end plates of each of the prosthetic discs have a length and a width, and wherein the length is greater than the width.

16. The kit of claim wherein the first and second end plates of the prosthetic discs have a length:width aspect ratio of the first and second end plates is in the range of about 1.5:1 to 5.0:1.

* * * * *